United States Patent [19]
Tiefenbrun et al.

[11] Patent Number: 5,470,320
[45] Date of Patent: Nov. 28, 1995

[54] METHOD AND RELATED DEVICE FOR OBTAINING ACCESS TO A HOLLOW ORGAN

[76] Inventors: Jonathan Tiefenbrun, 62 Country Rd., Mamaronek, N.Y. 10543; Peter J. Wilk, 185 W. End Ave., New York, N.Y. 10023

[21] Appl. No.: 866,760

[22] Filed: Apr. 10, 1992

[51] Int. Cl.⁶ .................................. 604N 264; 604N 280
[52] U.S. Cl. .............................. 604/174; 606/15
[58] Field of Search ..................... 604/174, 171, 604/180, 264, 280, 23, 26; 606/1, 15, 108, 170, 181; 128/DIG. 26, 749, 751, 753, 754

[56] References Cited

U.S. PATENT DOCUMENTS

| | | | |
|---|---|---|---|
| 1,998,225 | 4/1935 | Dow | 604/174 |
| 2,898,917 | 8/1959 | Wallace | 604/180 |
| 3,683,911 | 8/1972 | McCormick | 604/180 |
| 3,721,229 | 3/1973 | Panzer | 604/174 X |
| 3,989,033 | 11/1976 | Halpern et al. | 128/754 |
| 4,133,307 | 1/1979 | Ness | 604/180 X |
| 4,318,401 | 3/1982 | Zimmerman | 604/174 X |
| 4,616,631 | 10/1986 | Takahashi | 128/6 |
| 4,955,856 | 9/1990 | Phillips | 604/174 X |
| 4,986,825 | 1/1991 | Bays et al. | 606/170 X |
| 5,041,109 | 8/1991 | Abela | 606/15 |
| 5,215,521 | 6/1993 | Cochran et al. | 606/128 X |

*Primary Examiner*—Stephen C. Pellegrino
*Assistant Examiner*—Michael Peffley
*Attorney, Agent, or Firm*—Neil R. Sudol; Henry D. Coleman

[57] ABSTRACT

A method for obtaining access to a hollow organ of a patient comprises the steps of (i) providing a tubular member, (ii) pressing an end of the tubular member against a wall of the hollow organ, and (iii) removing a section of the organ wall surrounded by the tubular member, while maintaining the tubular member in engagement with the organ wall. The tubular member has a flange at the end which glued to the organ wall prior to the removal removal of the organ wall section. To remove the organ wall section an elongate instrument is inserted through the tubular member and operated to excise the organ wall section. An incision is made by cutting the organ wall with a laser or a blade. In either event, the excising instrument may be turned about an axis to form a closed circuit incision. The removal excised organ wall section is further implemented by securing the excised section of the organ wall to a distal end of the instrument, e.g., via suction or a hook element.

42 Claims, 4 Drawing Sheets

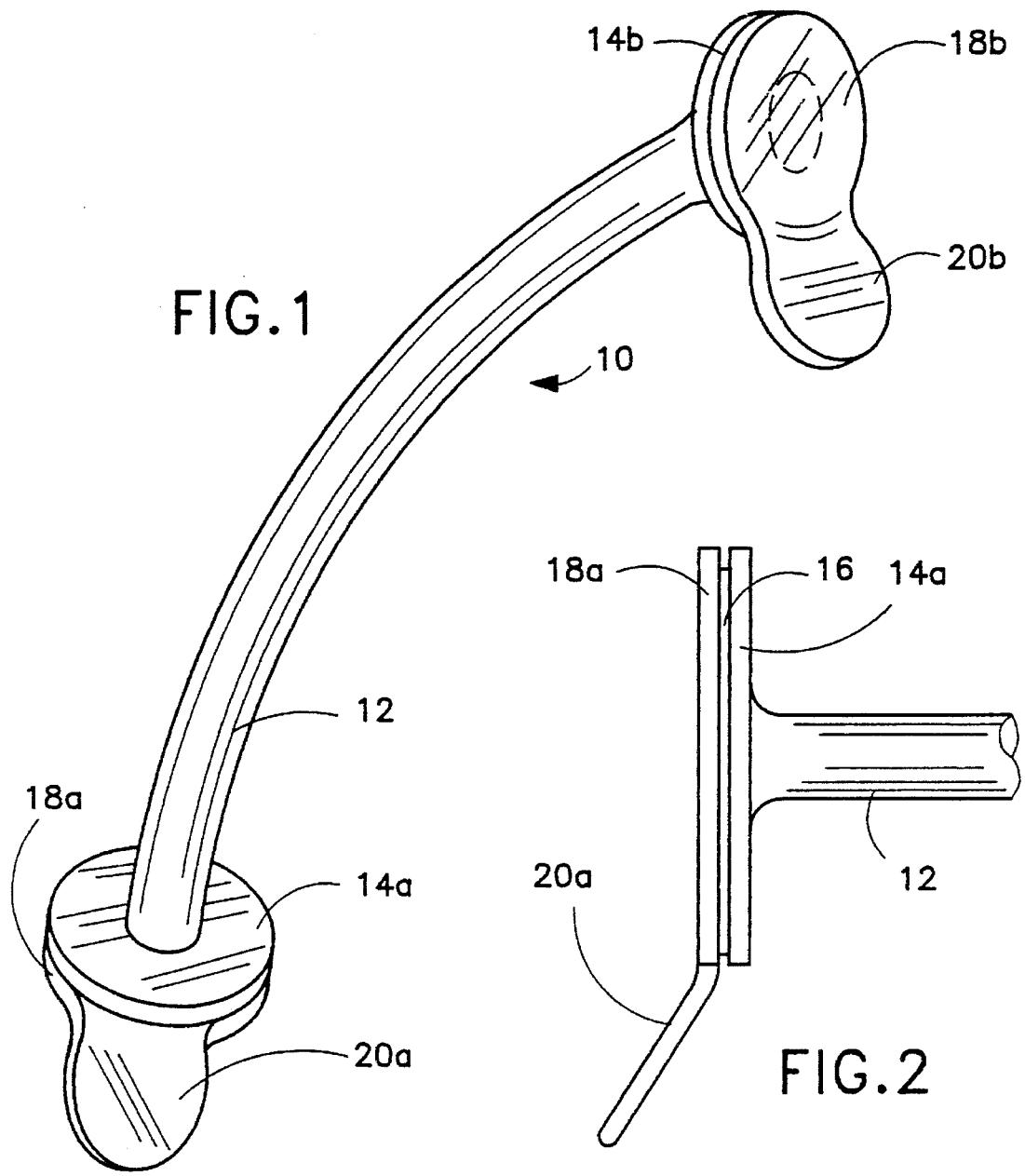
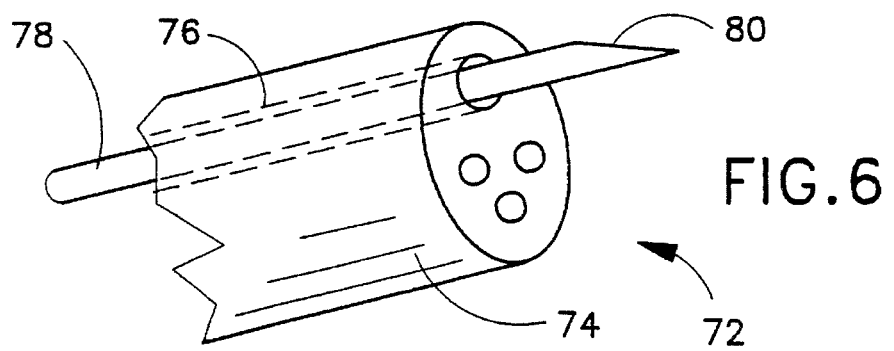

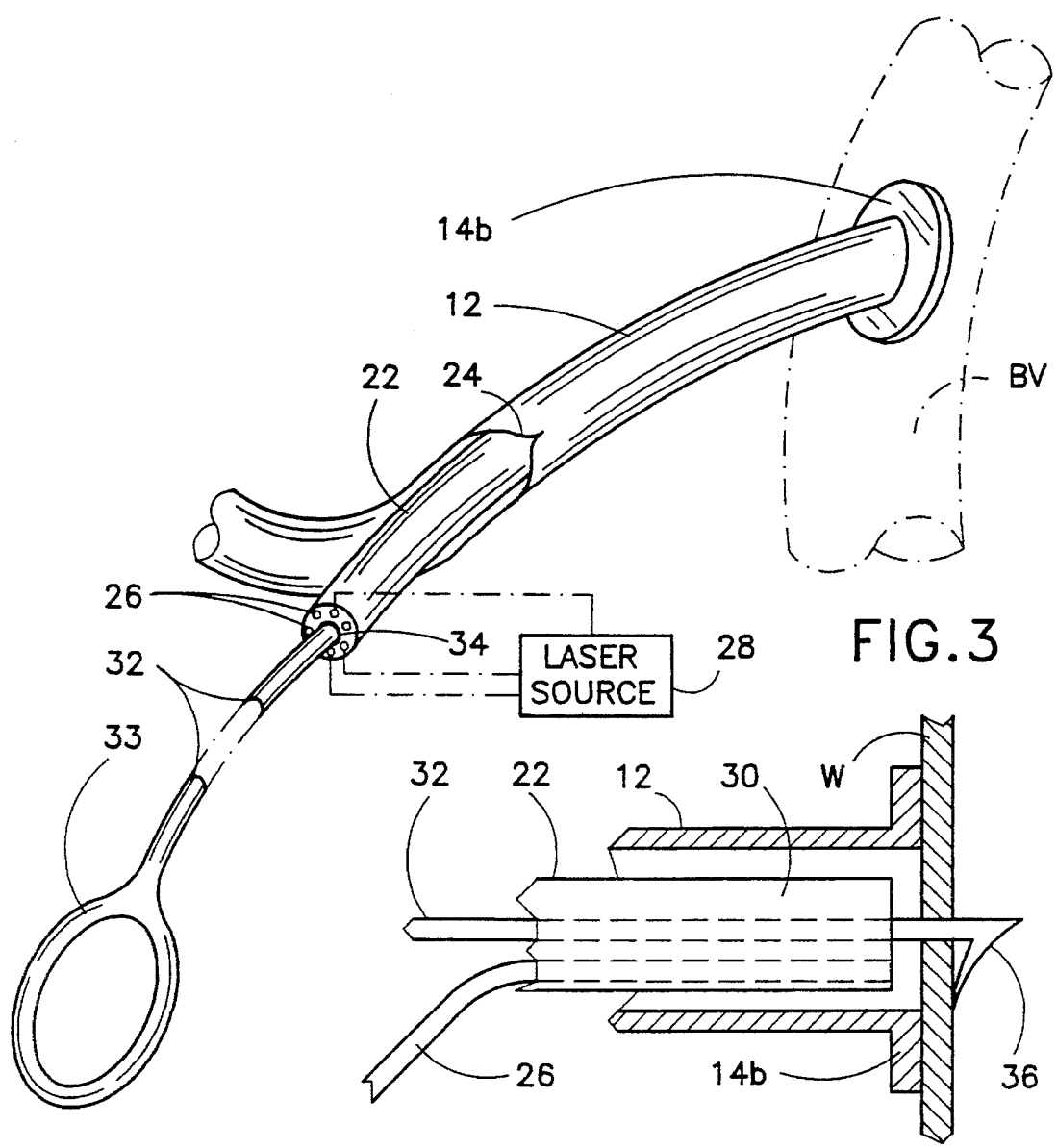
FIG.3
FIG.4
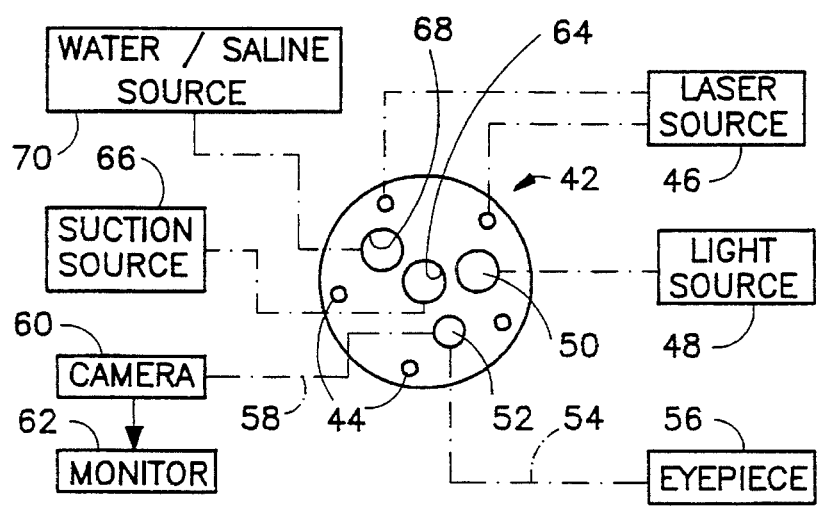
FIG.5

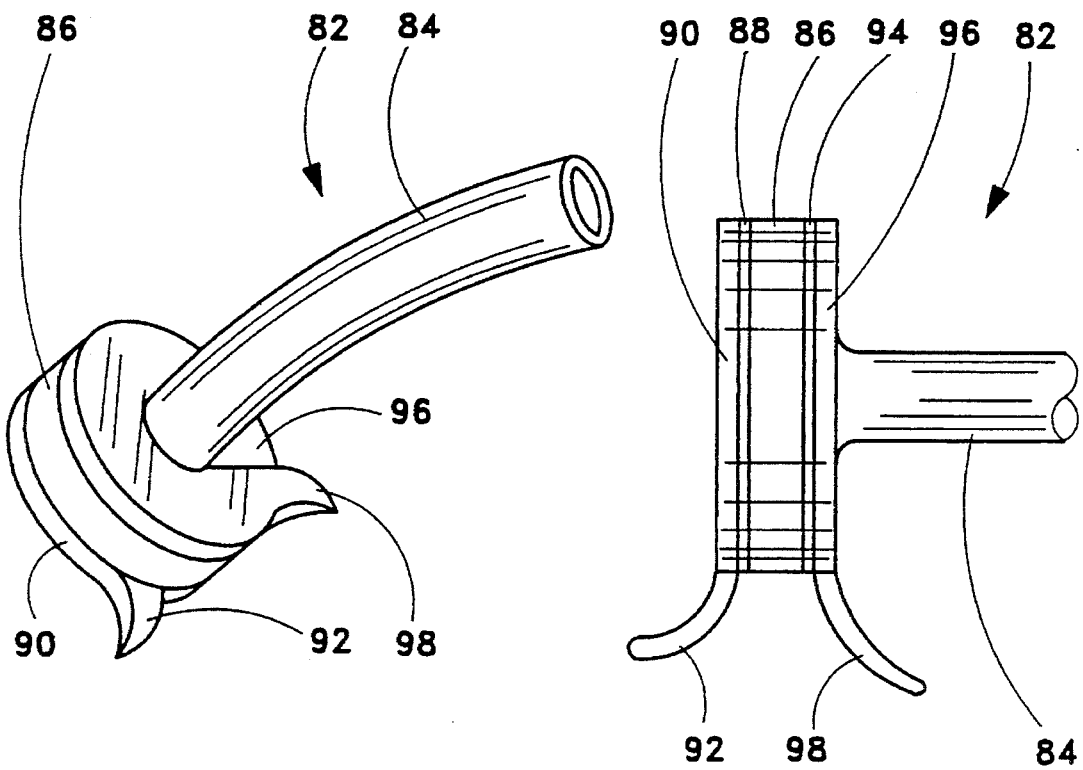
FIG.7
FIG.8
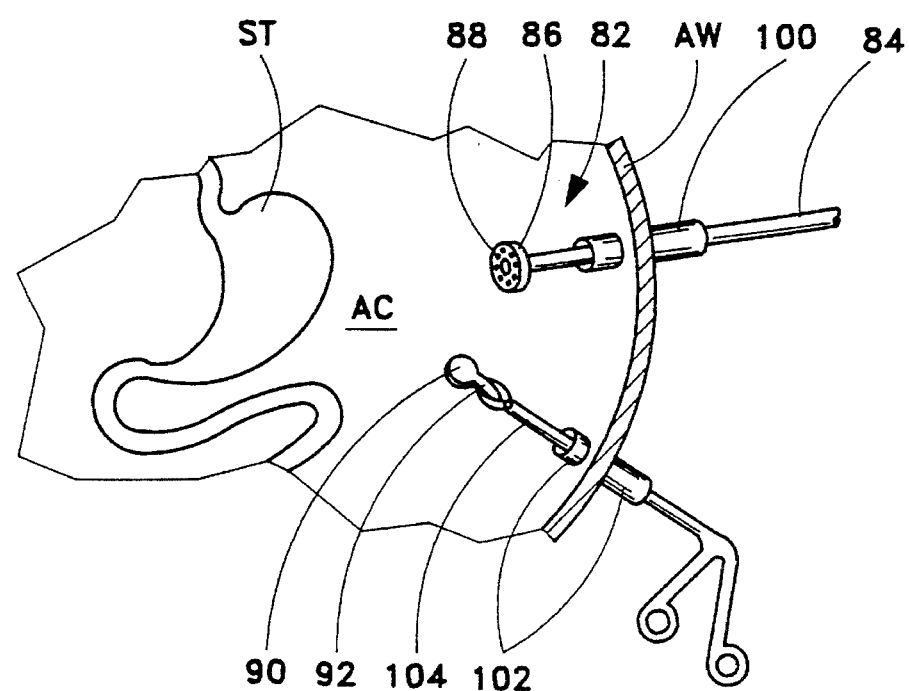
FIG.9A

METHOD AND RELATED DEVICE FOR OBTAINING ACCESS TO A HOLLOW ORGAN

BACKGROUND OF THE INVENTION

This invention relates to a method and an associated device or instrument assembly for obtaining access to a hollow organ such as a blood vessel or a stomach. This invention also relates to a method and an associated device or instrument assembly for forming a vacular bypass or for performing a gastrostomy and other, similar surgical operations.

Some common vascular disorders arise from the deposition of calcified materials in arteries to form blockages. Such blockages can sometimes greatly restrict the flow of blood and must either be removed or bypassed. In a bypass operation, a tubular prosthetic device or a vascular graft is attached to the affected artery at points upstream and downstream of the deposit, thereby shunting the blood flow past the obstruction. The attachment is typically implemented via sutures, the placement of which is understandably a laborious and time consuming procedure.

Other methods of attaching organic tissues to one another are known. Staples are frequently used, for example, in forming anastomoses. In addition, biologically effective adhesives are known which are biocompatible and nontoxic and capable of forming joints between organic tissues, as well as between biologic tissues and prosthetic implants. Such adhesives have been used in surgical procedures by applying the adhesive to one or more tissues or prosthetic devices via a brushing technique and pressing the tissues and/or prosthetic devices together.

In a gastrostomy, a tube is inserted into the stomach to feed nutrients thereto or to drain the stomach. Tubes may also be inserted into the urinary bladder (cystostomy), the gall bladder (cholecystostomy), the small intestine (jejeunostomy) or the cecum (cecostomy). In a gastrostomy, a jejeunostomy or a cecostomy, the conventional procedures, which involve piercing a wall of the respective organ, frequently results the spillage of digestive matter into the abdominal cavity. This spillage is dangerous insofar as it can lead to infection. An improved technique for obtaining access to such hollow organs is needed.

OBJECTS OF THE INVENTION

An object of the present invention is to provide a method for forming a vascular bypass.

A more particular object of the present invention is to provide such a method which is easier and quicker than conventional techniques.

Another object of the present invention is to provide a device or instrument assembly for facilitating the instatement of a vascular bypass.

Another, more general, object of the present invention is to provide a surgical method for obtaining access to a hollow organ.

A further object of the present invention is to provide a device or instrument assembly for facilitating the formation of an access port through the wall of a hollow organ.

Another, more specific, object of the present invention is to provide a method for use in performing a gastrostomy, a jejeunostomy or a cecostomy which reduces, if not eliminates, the chances of infection as discussed above.

SUMMARY OF THE INVENTION

A device for obtaining access to a hollow organ of a patient comprises, in accordance with the present invention, a tubular member made of a nontoxic biocompatible material and a flange provided at one end of of the tubular member, the flange also being made of a nontoxic biocompatible material.

Preferably, a layer of a nontoxic biocompatible adhesive is provided on a surface of the flange opposite the tubular member.

Such a device may be used, for example, to form a vacular bypass. Also, the device may be used in a gastrostomy.

According to another feature of the present invention, the device further comprises an elongate instrument inserted into the tubular member, the instrument being provided at a distal end with a laser port or a cutting blade or other element for excising a section of an organ wall to which the flange is attached.

Pursuant to another feature of the present invention, the instrument is further provided at the distal end with a suction port or a hook or other attachment element for securing an excised tissue section to the distal end of the instrument, whereby the excised tissue section may be removed from the tubular member along with the instrument.

Where the attachment element takes the form of a hook, the hook may be provided at the distal end of an elongate rod inserted through a longitudinal channel in the instrument. In that manner the hook may be manipulated independently of the instrument to insert the hook through the organ wall and subsequently to pull the excised tissue section back against the distal end of the instrument.

The instrument may in part take the form of an angioscope provided with light guides for conducting electromagnetic radiation into the tubular member and out again to enable a visual inspection of the organ wall inside the tubular member. Such an instrument is preferably flexible.

Pursuant to another feature of the present invention, the device further comprises a temporary cover sheet removably attached to the adhesive layer on a side thereof opposite the attachment flange. The cover sheet is advantageously provided with a pull tab.

In the event that the device is being used as a vascular bypass, the tubular member is preferably provided at opposite ends with flanges each having a layer of nontoxic biocompatible adhesive. In attaching the second flange, the excising instrument is inserted through an incision or aperture in the wall of the tubular member. Of course, the aperture is closed prior to the shunting of blood through the tubular bypass member.

A method for obtaining access to a hollow organ of a patient comprises, in accordance with the present invention, the steps of (i) providing a tubular member, (ii) pressing an end of the tubular member against a wall of the hollow organ, and (iii) removing a section of the organ wall surrounded by the tubular member, while maintaining the tubular member in engagement with the organ wall.

Pursuant to a more specific embodiment of the present invention, the tubular member is attached to the organ wall prior to the removal of the organ wall section. Where the tubular member has a flange at the end, the flange is pressed against the organ wall and the flange is attached, e.g., adhesived, to the organ wall during that step of pressing.

Pursuant to another feature of the present invention, the removal of the organ wall section entails the steps of inserting an elongate instrument through the tubular member and operating the instrument to excise the section of the organ wall. An incision may be made by cutting the organ wall with a laser or a blade.

The step of removing advantageously includes the additional step of securing the excised section of the organ wall to a distal end of the instrument. To secure the organ wall section, a hook element may be inserted into or through the organ wall to hold the severed wall section to the instrument. Where the hook is provided at the end of a rod, the rod is slid in a distal direction through a longitudinal channel in the instrument so that the hook pierces the organ wall. Subsequently, the rod is pulled in the proximal direction to clamp the excised tissue or wall section to the distal end of the instrument via the hook.

Alternatively, the excised tissue section may be clamped to the distal end of the instrument via suction applied via an aperture at the distal end of the instrument.

Where the hollow organ is a blood vessel and the operation is a vascular bypass, the method further comprises the step of attaching another end of the tubular member to the blood vessel, thereby forming a bypass of a portion of the blood vessel.

An instrument for making an incision comprises, in accordance with the present invention, an elongate body member having a longitudinal axis, and a plurality of optical fibers extending longitudinally through the tubular body member, the optical fibers being angularly spaced from one another and disposed at a common distance from the axis.

The body member is preferably flexible and the optical fibers are angularly equispaced from each other.

A method for forming a vascular bypass in accordance with the present invention is easier and quicker than conventional techniques. The procedure is facilitated by the device or instrument assembly described above.

A method for performing a gastrostomy, comprising the steps of (i) inserting a distal end portion of a tubular member through a laparoscopic cannula into a patient's abdominal cavity, (ii) attaching a distal tip of the tubular member to a stomach wall of the patient, (iii) removing the cannula, (iv) attaching the tubular member to an abdominal wall of the patient, (v) removing a section of the stomach wall enclosed by the tubular member, and (vi) inserting an ancillary tube through the tubular member into the patient's stomach.

The steps of attaching include the step of gluing the tubular member to the patient's stomach wall and abdominal wall. Where the tubular member has a flange, the flange may be provided with an adhesive layer on opposite sides to effectuate a bonding of the flange to the stomach and the abdominal wall.

It is to be noted that a similar technique may be used, for example, to obtaining an access port to the colon to enable a removal of the contents thereof. This technique reduces, and perhaps effectively eliminates, the chances of infection due to spillage of fecal matter into the abdominal cavity. There is never an opportunity for the contents of the colon (or the stomach, in a gastrostomy) to enter any part of the body other than the colon.

BRIEF DESCRIPTION OF THE DRAWING

FIG. 1 is a perspective view, on an enlarged scale, of a tubular vascular bypass member in accordance with the present invention.

FIG. 2 is a partial side elevational view, on a larger scale, of the vascular bypass member of FIG. 1.

FIG. 3 is a schematic perspective view, on an enlarged scale, of the vascular bypass member of FIGS. 1 and 2, showing an excision instrument inserted into the bypass member for excising a portion of an artery wall.

FIG. 4 is a cross-sectional view of the vascular bypass member and excision instrument of FIG. 3.

FIG. 5 is a distal end elevational view, on an enlarged scale, of a modified excision instrument in accordance with the present invention.

FIG. 6 is a partial perspective view, on an enlarged scale, of the distal end of another excision instrument in accordance with the present invention.

FIG. 7 is a partial perspective view, on an enlarged scale, of a tubular member for use in a gastrostomy procedure in accordance with the present invention.

FIG. 8 is a partial side elevational view, on a larger scale, of the tubular member of FIG. 7.

FIGS. 9A–9C are diagrams showing successive steps in the use of the tubular member of FIGS. 7 and 8 to perform a gastrostomy in accordance with the present invention.

DETAILED DESCRIPTION

Figure 9B:
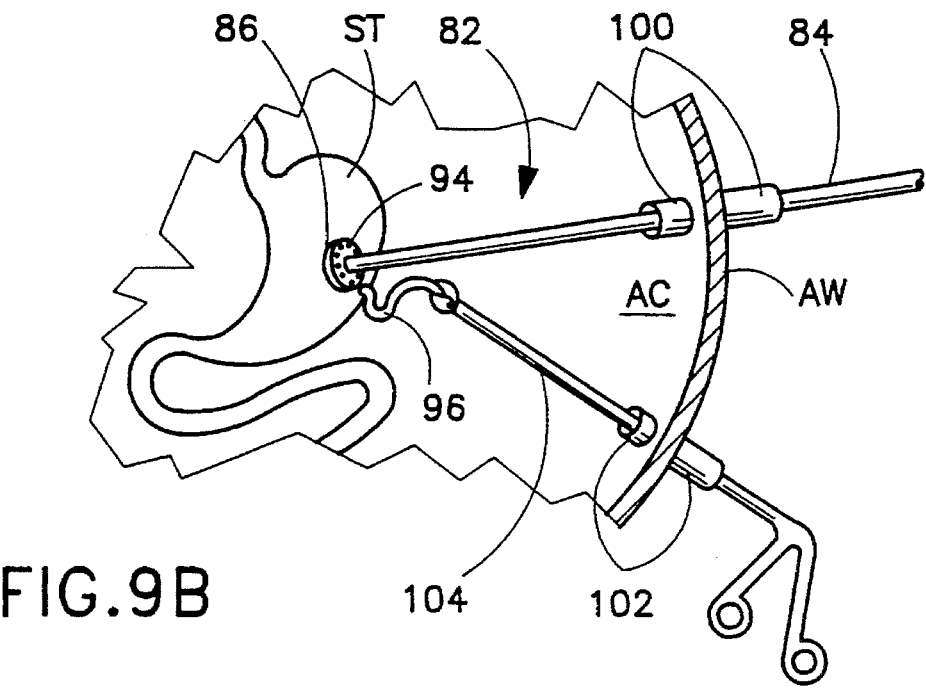

As illustrated in FIGS. 1 and 2, a device 10 for use in providing a patient with a vascular bypass comprises a tubular member 12 made of any nontoxic biocompatible material used in conventional surgical applications. Tubular member 12 is provided at opposite ends with integral annular flanges 14a and 14b. Flanges 14a and 14b in turn are each provided, on a surface facing opposite tubular member 12, with a layer 16 of a nontoxic biocompatible adhesive.

Device 10 further comprises cover sheets or membranes 18a and 18b removably attached to flanges 14a and 14b for protecting the adhesive layers 16. Each cover sheet 18a and 18b is provided with a respective pull tab 20a or 20b.

In using vascular bypass device 10, pull tab 20a or 20b is grasped to remove cover sheet 18a or 18b from its respective flange 14a or 14b, thereby exposing the underlying adhesive layer 16. The adhesive layer 16 of selected flange 14a or 14b is then pressed against a wall of a vein or, more likely, an artery so that flange 14a or 14b adheres to the artery wall.

As illustrated in FIG. 3, an elongate flexible excision instrument 22 is then inserted into tubular member 12 via an incision 24 in the wall thereof. Incision 24 may be formed during the surgical procedure or may be previously provided in tubular member 12, e.g., during manufacture. Alternatively, excision instrument 22 may be inserted through tubular member 12 from a proximal end.

Excision instrument 22 is longitudinally traversed by a plurality of optical fibers 26 which are connected at a proximal end of the instrument to a laser source 28. Source 28 generates a laser beam having a frequency or wavelength absorbed by vascular tissue.

Optical fibers 26 are angularly equispaced about the periphery of excision instrument 22. Upon an attachment of tubular member 12 to a wall W (FIG. 4) of an artery or blood vessel BV (FIG. 3) and an insertion of excision instrument 22 into tubular member 12 so that a distal end 30 of the instrument is juxtaposed to wall W, as illustrated in FIG. 4, laser source 28 is energized to transmit electromagnetic radiation of a predetermined frequency along optical fibers 26 to wall W. Excision instrument 22 is turned about a longitudinal axis (not illustrated) through an angular distance essentially equal to the angle between optical fibers 26, thereby forming a circular closed circuit incision in arterial wall W.

Prior to the activation of laser source 28, a rod 32 having a finger loop 33 at a proximal end is inserted in a distal direction through a longitudinal channel 34 in excision instrument 22 so that a hook 36 at the distal end of the rod pierces through arterial wall W, as depicted in FIG. 4. Hook 36 serves the function of holding the excised tissue section against the distal end 30 of excision instrument 22 and thereby preventing that piece of the arterial wall W from falling away into artery BV. Accordingly, upon an activation of laser source 28 and a turning of excision instrument 22 about its longitudinal axis, rod 32 is pulled in the proximal direction, i.e., away from arterial wall W, so that hook 36 clamps the excised arterial wall section against distal end 30 of excision instrument 22.

Upon the attachment of vascular bypass device 10 to arterial wall W and the removal of excision instrument 22 together with the excised arterial wall section clamped thereto, the other end of vascular bypass device 10 is attached to another segment of artery BV in an identical procedure, thereby essentially completing the bypass operation.

As illustrated in FIG. 5, a modified excision instrument 42 is longitudinally traversed by a plurality of angularly equispaced optical fibers 44 which are connected at a proximal end of the instrument to a laser source 46. A light source 48 is connected to another optical fiber or fiber optic bundle having an output port 50. Light source 48 generates visible electromagnetic radiation transmitted to output port 50 for illuminating a section of arterial wall inside tubular member 12. Reflected radiation is conducted through an inlet port 52 along an ordered fiber optic bundle 54 to an eyepiece 56. Alternatively, the reflected radiation is transmitted along an optic fiber bundle 58 to a camera 60, for example, a charge coupled device (CCD), which is connected to a video monitor 62 for displaying a video image of the vascular tissues enclosed at the distal end of tubular member 12 during a vascular bypass procedure.

Excision instrument 42 is further provided with a first longitudinally extending channel 64 for enabling the securing of an excised tissue section to the distal end of excision instrument 42. Channel 64 is operatively connected to a suction source or vacuum generator 66 for generating a negative pressure at the distal end of excision instrument 22. Alternatively, a rod with a hook such as rod 32 with hook 36 (FIGS. 2 and 4) may be inserted through channel 64.

Excision instrument 22 has another longitudinal channel or duct 68 connected to a water or saline source 70 for ejecting water through tubular member 12 in the event that channel 64 is traversed by rod 32.

As depicted in FIG. 6, another excision instrument 72 for use with tubular member 12 comprises a flexible body member 74 provided with a peripheral channel 76 which is longitudinally traversed by a rod 78 having a scalpel type blade 80 at a distal end. Blade 80 is used to form a circular incision in an arterial wall, e.g., wall W, during a turning of body member 74 about a longitudinal axis.

It is to be noted that excision instrument 22, 42 or 72 may take the form of an angioscope modified in accordance with principles set forth herein.

As illustrated in FIGS. 7 and 8, a device 82 for use in a gastrostomy procedure comprises a tubular member 84 made of any nontoxic biocompatible material used in conventional surgical applications. Tubular member 84 is provided at a distal end with an integral annular flange 86. Flange 86 is in turn provided, on a surface facing opposite tubular member 84, with a layer 88 (FIG. 8) of a nontoxic biocompatible adhesive removably covered with a protective film 90. Film 90 has a pull tab extension 92. On a side opposite adhesive layer 88 and film 90, flange 86 is provided with another layer 94 of nontoxic biocompatible adhesive temporarily covered with a protective release strip 96. Release strip 96 has a pull tab extension 98.

As illustrated in FIG. 9A, the distal end of tubular member 84 is inserted into a patient's abdominal cavity AC through a trocar sleeve or laparoscopic cannula 100 which has been previously inserted in the an abdominal wall AW of the patient. Through another trocar sleeve or laparoscopic cannula 102, a grasping forceps 104 is inserted. Tubular member 84 and forceps 104 are manipulated from outside the patient to remove protective film 90 from flange 86, thereby exposing adhesive layer 88.

As depicted in FIG. 9B, tubular member 84 is then manipulated to press flange 86 against a wall of a stomach ST so that the flange is attached thereto by adhesive layer 88. Upon the attachment of flange 84 to the stomach wall, forceps 104 is used to remove protective release strip 96 from the posterior side of flange 84. At that juncture, cannula 100 is removed from abdominal wall AW and, in the event that abdominal cavity AC had been filled with carbon dioxide or other biologically inert gas, the gas is allowed to escape from the abdominal cavity, whereupon abdominal wall approaches stomach ST. Tubular member 84 is then pulled in the proximal direction, i.e., out of abdominal cavity AC and through abdoominal wall AW, until posterior adhesive layer 94 is brought into contact with abdominal wall AW, as illustrated in FIG. 9C.

Figure 9C:
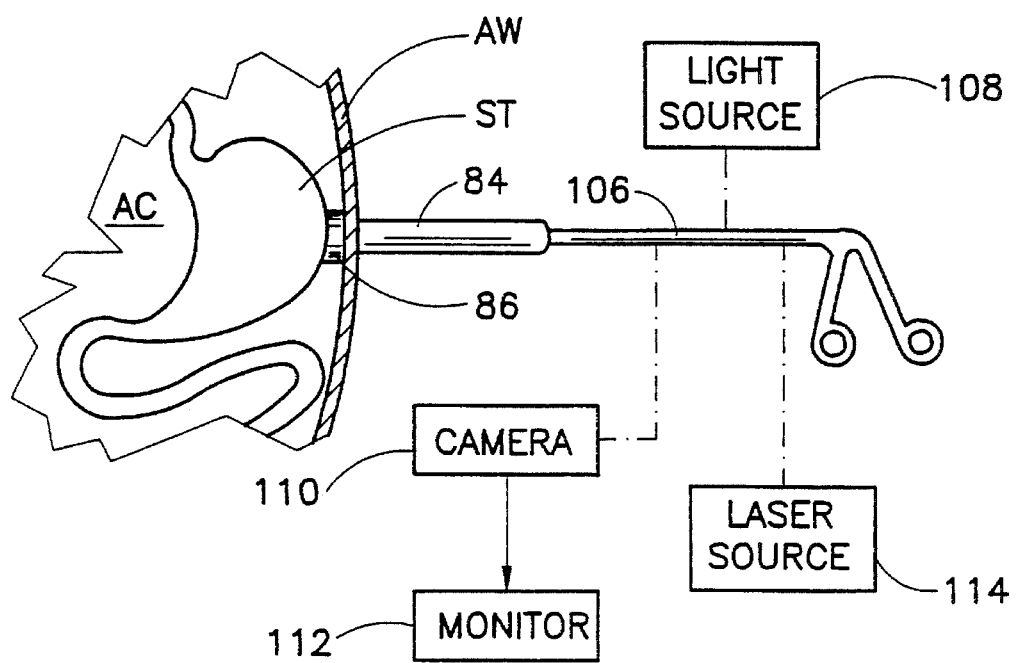

As further shown in FIG. 9C, an excision instrument 106 is then inserted through tubular member 84. Excision member 106 may take any form described hereinabove. For example, excision instrument 106 may be operatively connected to a light source 108, a camera 110 and a monitor 112 for enabling a visual inspection of a section of the stomach wall enclosed inside the distal end of tubular member 84 and flange 86. A laser source 114 may be connected to the instrument for use in forming a circular incision in the stomach wall at the distal end of tubular member 84.

Upon a removal of instrument 106 and the excised stomach wall section, as described hereinabove, a tube (not shown) may be inserted through tubular member 84 for purposes of draining stomach ST or feeding a supply of nutrients thereto.

Adhesives which may be utilized with the present invention include cyanoacrylic compositions and fibrin glues or sealants such as TISSUCOL™ and BERIPLAST™. Other adhesives will be known to one skilled in the art.

Although the invention has been described in terms of particular embodiments and applications, one of ordinary skill in the art, in light of this teaching, can generate additional embodiments and modifications without departing from the spirit of or exceeding the scope of the claimed invention. For example, a tubular bypass member in accordance with the present invention may be a graft fabricated from organic tissue instead a synthetic biocompatible material. In addition, the organic biocompatible adhesive may be applied to terminal flange-like appurtenances of the vascular bypass device via a brush immediately prior to application. In most instances, however, the releaseable protective strip or cover element is considered to be easier and safer to use.

It is to be noted, furthermore, that the method described herein may be used not only for vascular bypass operation or a gastrostomy but also for attaching tubular access port elements to other hollow organs of a patient, such as the gall bladder (cholecystostomy), the urinary bladder (cystostomy), the small intestine (jejeunostomy), and the cecum (tube cecostomy).

The flanges of a tubular access device may be attached to a hollow organ in some cases by other techniques such as laser welding, ultrasonic welding, cauterization, or suturing.

Accordingly, it is to be understood that the drawings and descriptions herein are proferred by way of example to facilitate comprehension of the invention and should not be construed to limit the scope thereof.

What is claimed is:

1. A device for obtaining access to a hollow organ of a patient, comprising:
   a tubular member made of a nontoxic biocompatible material;
   a flange also made of a nontoxic biocompatible material, said flange being connected to said tubular member at one end thereof; and
   an elongate instrument inserted into said tubular member, said instrument being provided at a distal end with means for excising a section of an organ wall to which said flange is attached via said layer of adhesive.

2. The device defined in claim 1, further comprising a layer of a nontoxic biocompatible adhesive on a surface of said flange opposite said tubular member.

3. The device defined in claim 2, further comprising a temporary cover sheet removably attached to said layer on a side thereof opposite said flange.

4. The device defined in claim 2 wherein said tubular member is provided at an end opposite said flange with an additional flange having a respective layer of nontoxic biocompatible adhesive.

5. The device defined in claim 3 wherein said cover sheet is provided with a pull tab.

6. The device defined in claim 1 wherein said means for excising includes an outlet of an optical fiber for directing a laser beam at the organ wall.

7. The device defined in claim 1 wherein said means for excising includes a blade.

8. The device defined in claim 1 wherein said instrument is further provided at said distal end with attachment means for securing an excised tissue section to said distal end, whereby said excised tissue section may be removed from said tubular member along with said instrument.

9. The device defined in claim 8 wherein said attachment means includes a hook.

10. The device defined in claim 9 wherein said instrument includes a longitudinal channel, said hook being disposed at the distal end of an elongate rod inserted through said channel.

11. The device defined in claim 8 wherein said attachment means includes a suction aperture.

12. The device defined in claim 1 wherein said instrument is provided with means for enabling a visual inspection of said organ wall.

13. The device defined in claim 1 wherein said instrument is flexible.

14. The device defined in claim 1 wherein said flange is annular.

15. The device defined in claim 1 wherein said tubular member is flexible.

16. A method for obtaining access to a hollow organ of a patient, comprising the steps of:
   providing a tubular member;
   pressing an end of said tubular member against a wall of the hollow organ; and
   removing, through said tubular member, a section of the organ wall enclosed by said tubular member, while maintaining said tubular member in engagement with said organ wall.

17. The method defined in claim 16 wherein said tubular member has a flange at said end, said step of pressing including the step of pressing said flange against said organ wall.

18. The method defined in claim 17, further comprising the step of attaching said flange to said organ wall during said step of pressing.

19. The method defined in claim 18 wherein said step of attaching includes the step of gluing said flange to said organ wall.

20. The method defined in claim 18 wherein said hollow organ is a stomach, further comprising the steps of (a) providing a trocar sleeve and an ancillary tube, (b) disposing said trocar sleeve in a patient's abdominal wall during a laparoscopic procedure, (c) inserting a distal end portion of said tubular member into the patient's abdomen via said trocar sleeve, (d) attaching said flange to an abdominal wall of the patient, and (e) inserting said ancillary tube through said tubular member into the patient's stomach.

21. The method defined in claim 18 wherein said hollow organ is an artery or a vein, further comprising the step of attaching another end of said tubular member to said artery or vein, thereby forming a bypass of a portion of said artery or vein.

22. The method defined in claim 16 further comprising the step of providing an elongate instrument having means at a distal end for excising said section of said organ wall, said step of removing including the steps of inserting said elongate instrument through said tubular member and operating said instrument to excise said section of said organ wall.

23. The method defined in claim 22 wherein said step of removing further includes the step of securing the excised section of said organ wall to a distal end of said instrument.

24. The method defined in claim 23 wherein said instrument is provided at said distal end with a hook element, said step of securing including the steps of inserting said hook element into said organ wall and holding said severed wall section to said instrument via said hook element.

25. The method defined in claim 23 wherein said instrument is provided at said distal end with an aperture, said step of securing including the step of applying suction to said severed section via said aperture.

26. The method defined in claim 24 wherein said hook element is disposed at the distal end of a rod slidably inserted through said instrument, said step of securing further comprising the step of pulling said rod in a proximal direction to clamp said severed section against the distal end of said instrument.

27. The method defined in claim 16 wherein said hollow organ is taken from the group including a blood vessel, a stomach, a bladder and an intestine.

28. The method defined in claim 16, further comprising the step of attaching said end of said tubular member to said organ wall prior to said step of removing.

29. A method for obtaining access to a hollow organ of a patient, comprising the steps of;
   providing a tubular member having an end;
   further providing an elongate instrument provided at a distal end with incising means for forming an incision in organic tissues;
   bringing said end of said tubular member into engagement with a wall of a hollow organ;

sliding said elongate instrument longitudinally through said tubular member so that a distal end of said instrument is disposed proximately to the organ wall;

operating said incising means to form a closed circuit incision in said organ wall to sever a section thereof;

securing the severed section of said organ wall to the distal end of said instrument; and removing said instrument, together with the severed wall section attached to the distal end thereof, from said tubular member.

30. The method defined in claim 29, further comprising the step of attaching said tubular member to said organ wall prior to said step of sliding.

31. The method defined in claim 30 further comprising the step of providing a biocompatible and nontoxic adhesive, said tubular member being provided with a flange on said end, said step of attaching including the step of bonding said flange to said organ wall with said biocompatible and nontoxic adhesive.

32. The method defined in claim 29 wherein said incising means comprises an optical fiber outlet for directing a laser beam at said organ wall, further comprising the step of turning said instrument about a longitudinal axis during said step of operating.

33. The method defined in claim 29 wherein said instrument is provided at said distal end with a hook element, said step of securing including the steps of inserting said hook element into said organ wall and holding said severed wall section to said instrument via said hook element.

34. The method defined in claim 33 wherein said hook element is disposed at the distal end of a rod slidably inserted through said instrument, said step of securing further comprising the step of pulling said rod in a proximal direction to clamp said severed section against the distal end of said instrument.

35. The method defined in claim 29 wherein said instrument is provided at said distal end with an aperture, said step of securing including the step of applying suction to said severed section via said aperture.

36. A method for performing a gastrostomy, comprising the steps of:

providing a laparoscopic cannula and a tubular member having a distal end portion with a distal tip;

inserting said cannula in an abdominal wall of a patient;

further providing an elongate instrument provided at a distal end with incising means for forming an incision in organic tissues;

inserting said distal end portion of said tubular member through said laparoscopic cannula into an abdominal cavity of the patient;

attaching said distal tip of said distal end portion to a stomach wall of the patient;

removing said cannula;

attaching said tubular member to an abdominal wall of the patient;

removing a section of the stomach wall enclosed by said tubular member; and inserting an ancillary tube through said tubular member into the patient's stomach.

37. The method defined in claim 36 wherein said steps of attaching include the step of gluing said tubular member to the patient's stomach wall and abdominal wall.

38. A device for obtaining access to a hollow organ of a patient, comprising:

a tubular member made of a nontoxic biocompatible material;

a pair of flanges also made of a nontoxic biocompatible material, said flanges being connected to said tubular member at opposite ends thereof;

two layers of a nontoxic biocompatible adhesive predisposed on surfaces of said flanges opposite said tubular member; and a pair of cover sheets removably attached to said flanges over respective ones of said layers, to protect said layers prior to use.

39. A device for obtaining access to a hollow organ of a patient, comprising:

a tubular member made of a nontoxic biocompatible material;

a flange also made of a nontoxic biocompatible material, said flange being connected to said tubular member at one end thereof; and an elongate instrument inserted into said tubular member, said instrument being provided at a distal end with attachment means for securing an excised tissue section to said distal end, whereby said excised tissue section may be removed from said tubular member along with said instrument.

40. The device defined in claim 39 wherein said attachment means includes a hook.

41. The device defined in claim 40 wherein said instrument includes a longitudinal channel, said hook being disposed at the distal end of an elongate rod inserted through said channel.

42. The device defined in claim 39 wherein said attachment means includes a suction aperture.

* * * * *